United States Patent [19]

Downs

[11] Patent Number: 5,232,934
[45] Date of Patent: Aug. 3, 1993

[54] METHOD FOR THE TREATMENT OF PSYCHOMOTOR STIMULANT ADDICTION

[75] Inventor: David Downs, Ann Arbor, Mich.

[73] Assignee: Warner-Lambert Co., Morris Plains, N.J.

[21] Appl. No.: 916,776

[22] Filed: Jul. 17, 1992

[51] Int. Cl.⁵ ............................................. A61K 31/44
[52] U.S. Cl. ..................................... 514/345; 514/812
[58] Field of Search .................................. 514/345, 812

[56] References Cited

U.S. PATENT DOCUMENTS

| | | | |
|---|---|---|---|
| 4,061,756 | 12/1977 | Hastings et al. | 424/263 |
| 4,067,983 | 1/1978 | Poschet et al. | 424/263 |
| 4,128,555 | 12/1978 | Butler | 546/290 |
| 4,386,094 | 5/1983 | Butler et al. | 424/263 |
| 4,434,169 | 2/1984 | Poschel et al. | 424/263 |
| 4,666,926 | 5/1987 | Mahjour et al. | 514/345 |
| 5,028,611 | 7/1991 | Halikas | 514/277 |
| 5,059,600 | 10/1991 | Gawin et al. | 514/253 |

OTHER PUBLICATIONS

Marriott et al "Effects of a New Cognition Activator, Cl-844, In Animal Models of Psychostimulant/Activity" 1 Mar. 1984.

Butler et al., "Cognition Activating Properties of 3 Aryloxy Pyridines," Mar. 1981, J MED CHEM 24(3), 346-350.

*Primary Examiner*—S. J. Friedman
*Assistant Examiner*—William Jarvis
*Attorney, Agent, or Firm*—Krass & Young

[57] ABSTRACT

A method of treatment is provided for reducing or eliminating psychomotor addiction in mammalian subjects, employing as an active agent 3-phenoxypyridine or a pharmaceutically acceptable acid-addition salt thereof.

5 Claims, 5 Drawing Sheets

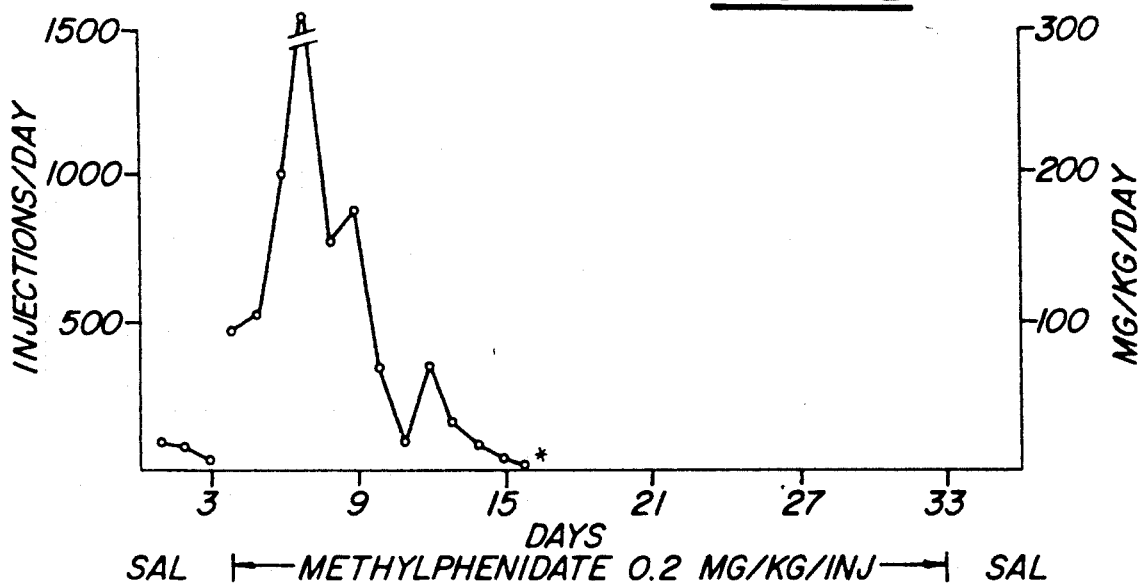
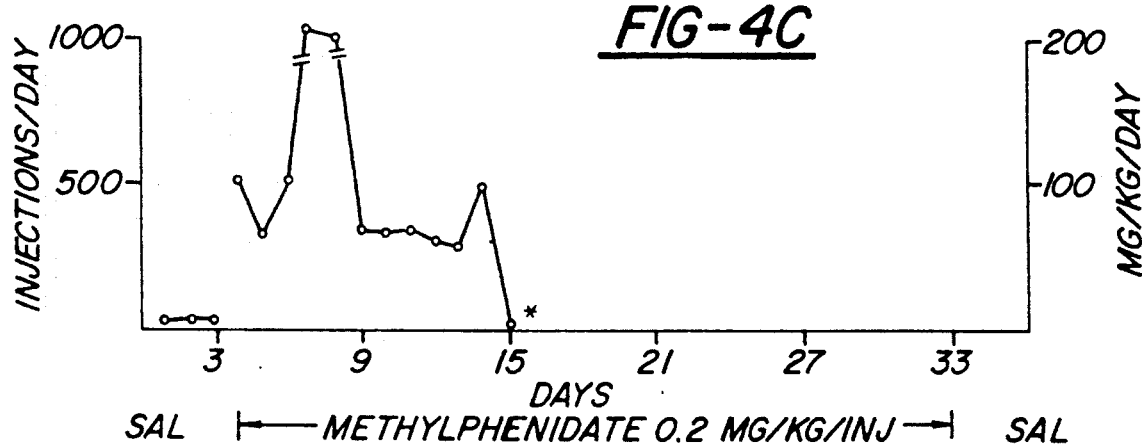
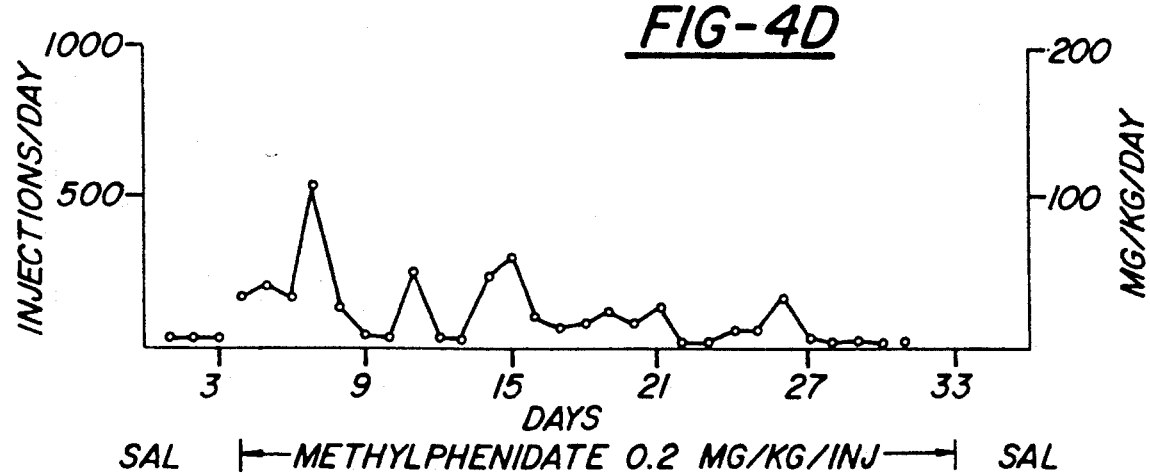

METHOD FOR THE TREATMENT OF PSYCHOMOTOR STIMULANT ADDICTION

FIELD OF THE INVENTION

This invention relates to a method for use employing 3-phenoxypyridine or a pharmaceutically acceptable acid-addition salt thereof, in the treatment of psychomotor stimulant addiction in mammalian subjects.

BACKGROUND OF THE INVENTION

Certain aspects of the abuse potential of drugs can be measured pharmacologically. These include the ability of a drug to act as a reinforcer, or to produce physical dependence, tolerance, and behavioral or somatic toxicity. Management of minimal brain dysfunction (MBD) involves the use of psychomotor stimulants such as amphetamine, cocaine, diethylpropion and the like, which produce little or no physical dependence, but do induce tolerance and intense psychotoxicity. These toxic effects can be quantitated in animal studies, e.g., by allowing monkeys the unlimited opportunity to self-inject drugs for prolonged periods. Under such conditions many monkeys will eventually take lethal doses of amphetamine, cocaine or diethylpropion.

Methods of treatment for reducing the use of psychomotor stimulants such as cocaine, amphetamine, methylphenidate, methamphetamine and the like are well known. For instance, U.S. Pat. No. 5,028,611 describes the use of carbamazepine as a replacement for reducing the use of psychomotor stimulants. U.S. Pat. No. 5,059,600 describes the use of flupenthixol as a replacement for treating drug habit disorders of the kind in question. It is known that the cognition activator compound, 3-phenoxypyridine monosulfate, does not share prominent pharmacological effects in rats with known psychomotor stimulant drugs, Marriott et al., Federation Proceedings, 43:571 (Abstract 1672). From U.S. Pat. No. 4,128,555 it is known that oral doses of 3-phenoxypyridine monosulfate produce only minimal signs of motor stimulation in rats. Other patents describing the use of 3-phenoxypyridine compounds are U.S. Pat. Nos. 4,061,756; 4,067,983; 4,128,555; 4,386,094; and 4,434,169.

SUMMARY OF THE INVENTION

It is an object of the invention to provide a method for reducing or eliminating the abusive use of psychomotor stimulants by addicted subjects that are dependent on these drugs. This is accomplished by administering a 3-phenoxypyridine compound to the addicted subject, which compound in dosage form I have found to be a safe substitute for the abused psychomotor stimulants.

DETAILED DESCRIPTION OF THE INVENTION

Figure 1A:
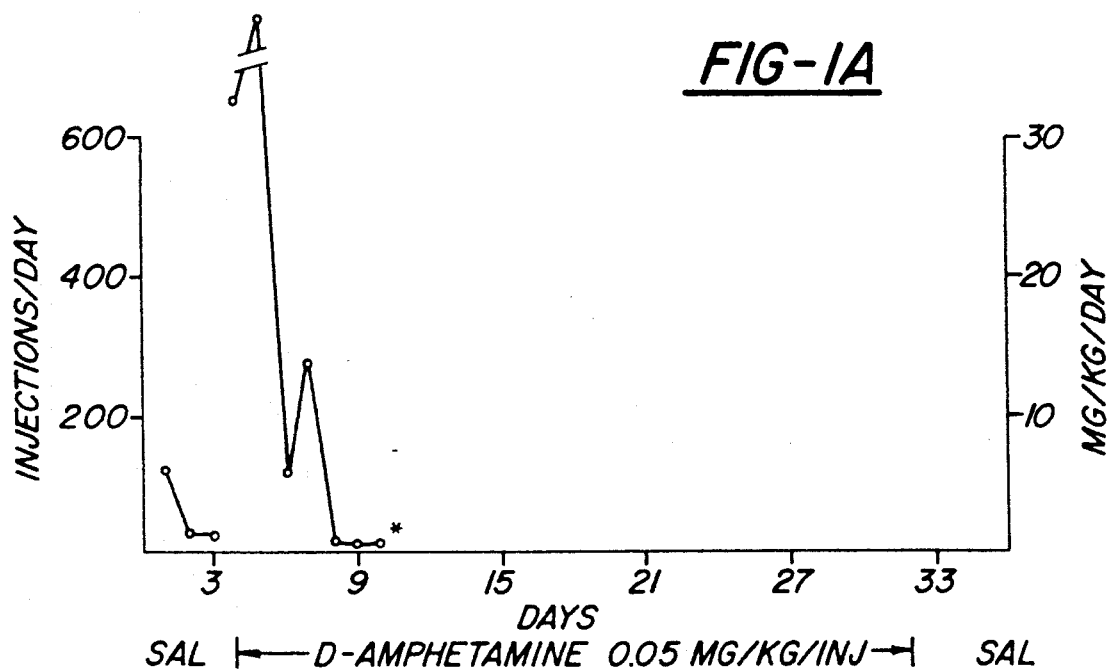
FIG. 1 is a plot in drug addiction animal studies of the number of injections and total amount of D-amphetamine self administered daily by four rhesus monkeys. Amphetamine was made available without time or dose limitation for 30 days preceded and followed by three days of access to saline. The asterisk indicates the death of monkey 6768. The dashed line denotes where the catheter in monkey 6722 became defective and was replaced.
Figure 1B:
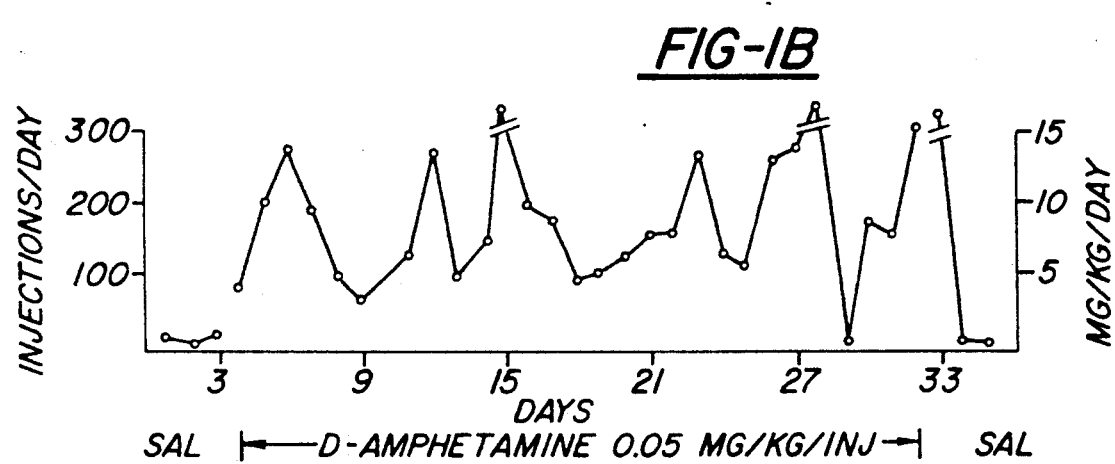
Figure 1C:
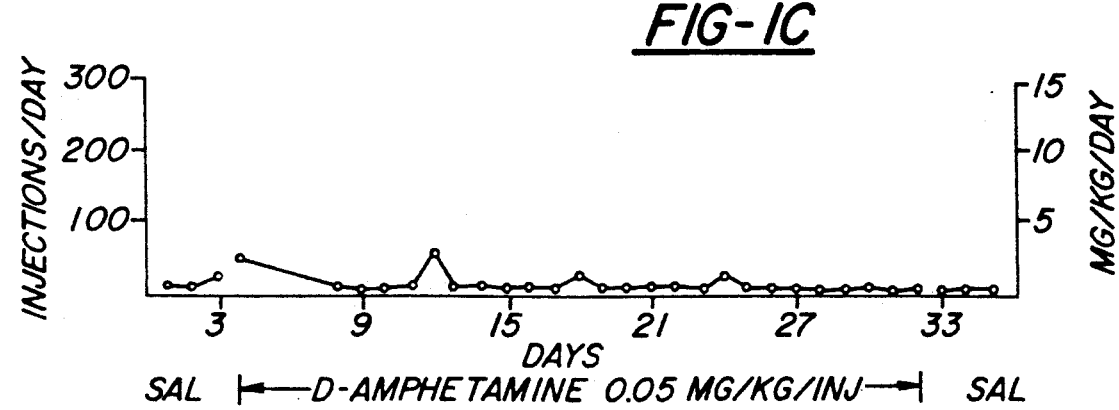
Figure 1D:
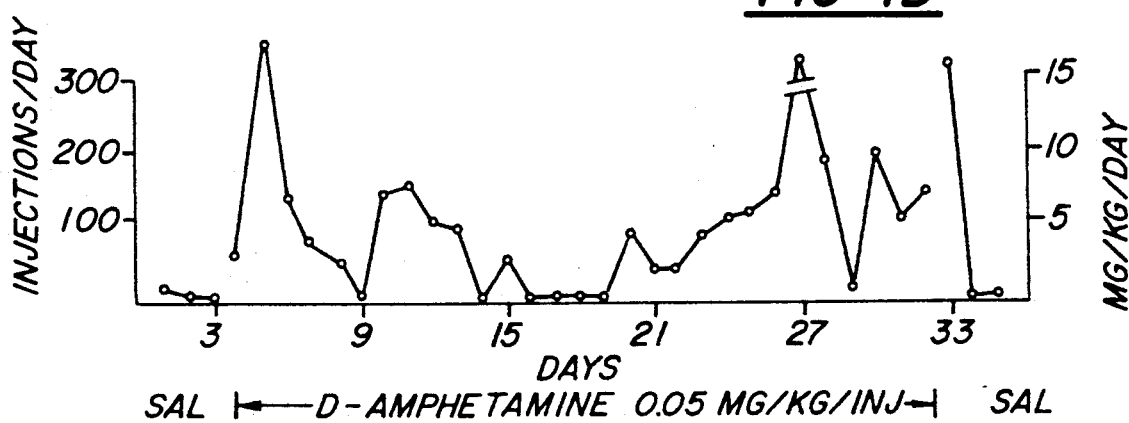

The method of the invention in a preferred embodiment comprises administering a pharmaceutically acceptable composition in dosage form comprising as active agent an effective amount of 3-phenoxypyridine or, preferably a pharmaceutically acceptable salt thereof to a subject that is in need of reducing or eliminating the supportive use of a psychomotor stimulant.

Some typical examples of pharmaceutically acceptable acid-addition salt forms are the hydrochloride, monosulfate, hydrobromide, nitrate, citraconate, maleate, p-toluene sulfonate and methane sulfonate salts, a preferred salt being the monosulfate salt.

In addition, the 3-phenoxypyridine and its acid-addition salts can exist in anhydrous forms as well as in solvated, including hydrated, forms. In general, the hydrate forms and the solvated forms with pharmaceutically-acceptable solvents are equivalent to the anhydrous or unsolvated form for the purposes of the invention. A typical hydrate would be the aforementioned hydrochloride in the form of its hydrate.

In addition, 3-phenoxypyridine compounds may exist in more than one crystalline form, such as the monosulfate, m.p. 114.5°–117° C. and m.p. 107°–109° C., and all forms are intended to be included within the scope of this invention.

In accordance with the invention, oral pharmaceutical compositions are produced by formulating 3-phenoxypyridine or a pharmaceutically acceptable acid-addition salt thereof (as an active ingredient) in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being subdivided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The method of the invention is applicable to treatment of addiction to psychomotor stimulants in general and in particular to cocaine, amphetamine, methylphenidate compounds and the like. For human subjects, administration is preferably oral. The usual mammalian dosage range for a 70 kg. subject, preferably in spaced or divided daily doses expressed as the free base, is from about 0.1 to about 400 mg/kg of 3-phenoxypyridine, preferably four times daily. Administration is continued daily until the abusive use is controlled, up to a maximum daily dosage of about 1600 mg/kg of body weight.

The effectiveness of the present method is seen in animal studies that assess the quality and intensity of toxicity produced by the unlimited self-administration of 3-phenoxypyridine monosulfate in comparison to D-amphetamine, cocaine and methylphenidate described as follows.

Thirteen rhesus monkeys (Macaca mulatta) were housed individually and restrained with a steel arm and harness system. Each monkey was surgically prepared with a silicone rubber catheter in the internal jugular vein. The distal end of the catheter exited through the skin of the back and connected to a tube which passed through the hollow restraining arm to a reciprocating syringe driver located outside the cage.

The monkeys were given 100 grams of monkey chow and one-half orange daily at 8 a.m.; uneaten chow was removed and weighed at 4 pm. Body weights were determined weekly. Videotape recordings were made both routinely and when unusual behavior was evident. Room lights were controlled to provide 12 hour diurnal cycles.

Each of the monkeys had served in previous self-administration studies with a variety of drugs although all animals had essentially comparable experimental histories. Saline had been made available for self-injection prior to each of the drugs tested in the current study.

The compositions tested were isotonic saline preparations containing, respectively, 3-phenoxypyridine monosulfate (0.5 mg/kg/injection), D-amphetamine sulfate (0.005 mg/kg/injection), cocaine hydrochloride (0.2 mg/kg/injection), and methylphenidate hydrochloride (0.2 mg/kg/injection). All dosages are expressed as the base.

Self-Administration Procedure

A transilluminated plastic button served as the response device. A two-inch long aluminum bar projected from the bottom of the button into the cage. One bar or button press activated the syringe driver to deliver 0.5 ml of solution through the catheter over five seconds followed by a five second refill. Responses during the infusion cycle had no consequence. Drug solutions were available for self-administration without time or dose limitations for 30 consecutive days. The numbers of self-injections were recorded from mechanical counters daily at 8 a.m.

Results

D-Amphetamine. Exposure to 0.05 mg/kg/injection amphetamine produced rapid increases in bar pressing behavior compared to saline (FIG. 1). Monkey 6768 took 127 mg/kg amphetamine within the first four days and was found comatose. No attempts were made to revive the monkey, and it was euthanized three days later. Microscopic examination of brain sections revealed extensive vacuolization about the small motor neurones throughout the cerebral cortex and cerebellar folia. This was particularly striking within the hippocampal gyrus.

Monkey 6722 self-administered about 3000 injections of amphetamine in the first few days, but the catheter was defective and the solution was being delivered subcutaneously. The catheter was replaced and thereafter this animal took only minimal amounts of drug (FIG. 1).

Monkeys 452 and 6736 continued to self-administer amphetamine with variable daily intake through the test period (FIG. 1). During periods of moderate to high rates of self-injection, toxicity was manifested in pronounced stimulation, anorexia, oral dyskinesias, stereotypy (rocking, pacing about or biting objects), and ataxia to the extent of staggering.

Food intake was reduced by about 40% during the first 10 days in the three monkeys which survived amphetamine self-administration. Thereafter, food consumption returned to maximum. Nevertheless, weight losses of 10 and 13% were noted for monkeys 452 and 6736 respectively at the end of the test period. Monkey 6722 lost about 7% in the first 10 days but gained it all back by the end of the study.

Figure 2A:
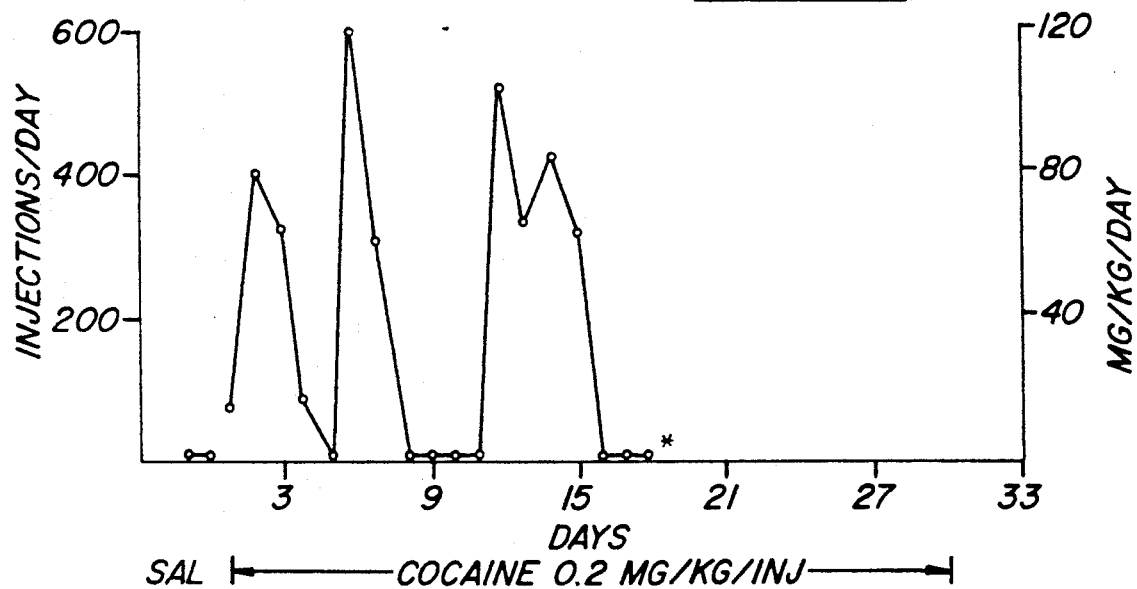
FIG. 2 is a plot of the number of injections and total amount of cocaine self-administered daily by three rhesus monkeys. Cocaine was made available without time or dose limitation for 30 days preceded by two days access to saline. Asterisks denote the deaths of monkeys 6736 and 465.
Figure 2B:
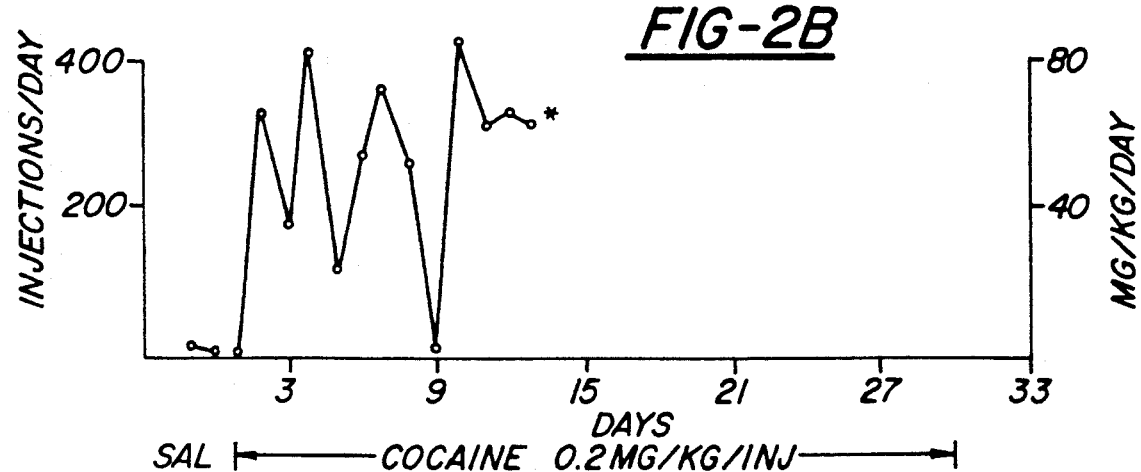
Figure 2C:
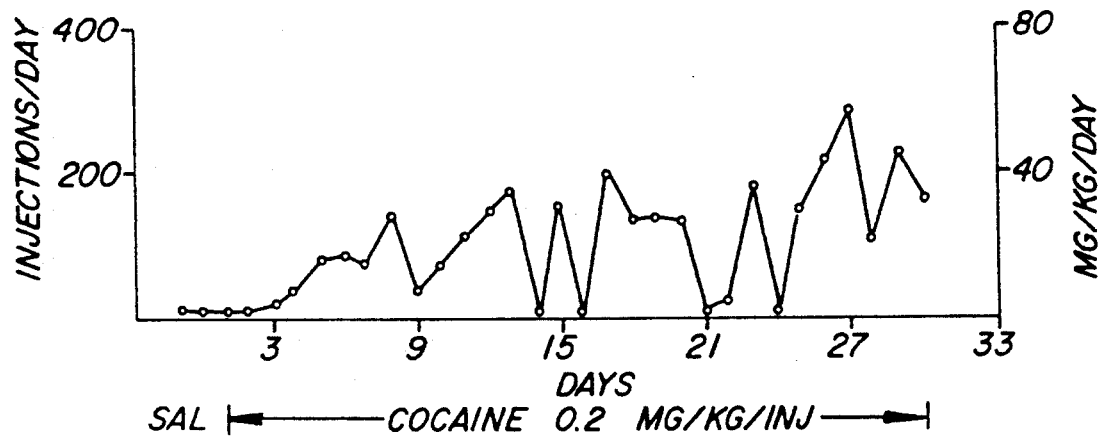
Figure 3A:
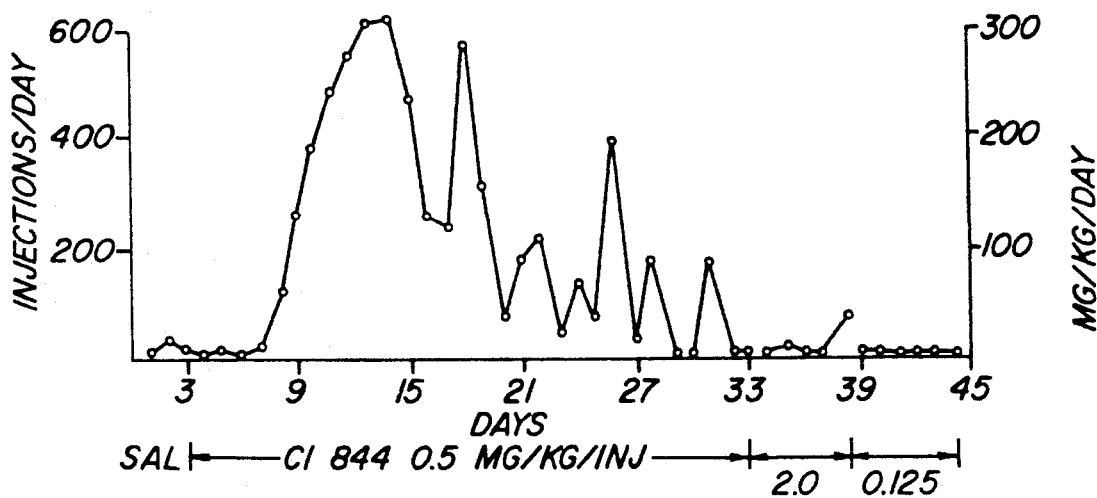
FIG. 3 is a plot of the number of injections and total amount of 3-phenoxypyridine monosulfate (CI-844) self-administered daily by four rhesus monkeys. It was made available without time or dose limitation for 30 days preceded by three days access to saline. The unit dose of 3-phenoxypyridine monosulfate was increased to 2 mg/kg/ injection from the 34th through the 38th day and then lowered to 0.125 mg/kg/injection from the 39th through the 44th day of the study. The dashed line (monkey 6764) denotes an intermittent malfunction of the mechanical counter from days 19 through 32. Drug self-administration was unaffected; however, daily intake could not be accurately determined during this period.
Figure 3B:
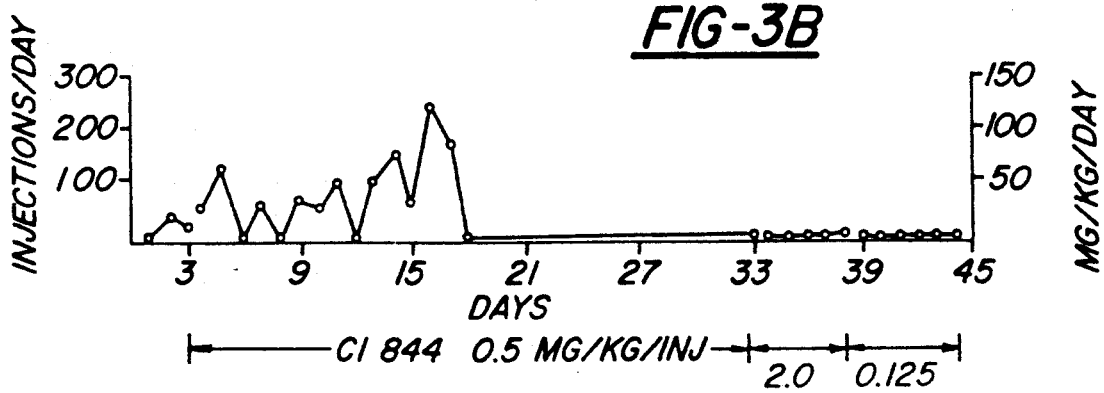
Figure 3C:
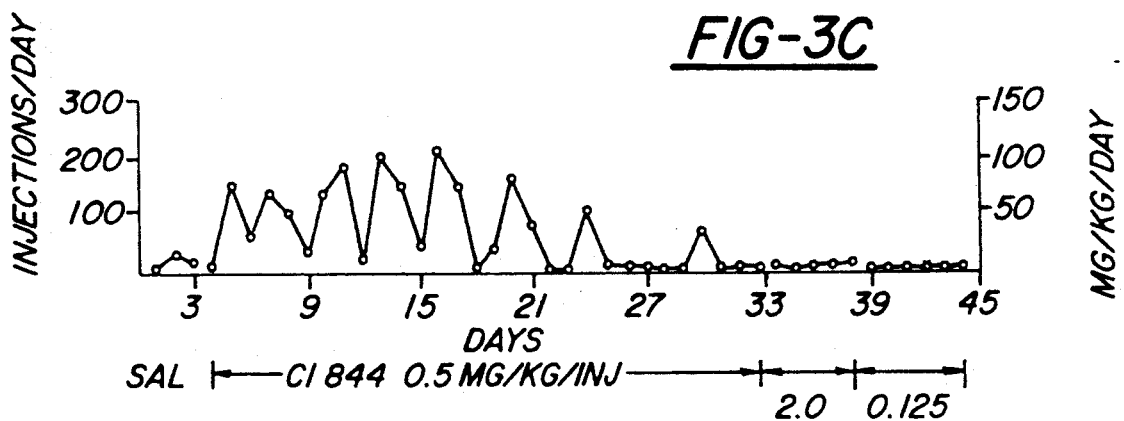
Figure 3D:
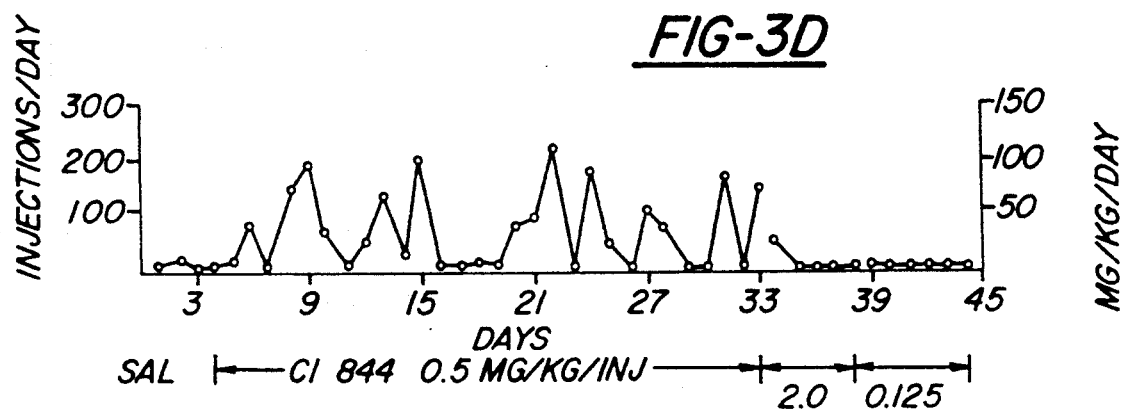

Cocaine. The three monkeys which survived the amphetamine exposure (6736, 452, 6722) were allowed to self-inject saline for three days and then were given access to 0.2 mg/kg/injection cocaine. All three monkeys took more injections of cocaine than saline (FIG. 2). On the 15th day of cocaine exposure, monkey 6736 became comatose and died two days later. Microscopic examination of brain sections obtained several hours post mortem disclosed pericellular vacuolation throughout the cortex, with marked vacuolation of those cells in the hippocampal gyrus. Liver sections showed a few portal foci of inflammation.

Monkey 452 died of apparent cardiac arrest induced on the 14th day during a routine purging of the catheter. Autopsy was performed immediately; liver and brain sections were submitted for histological inspection. The sections of brain disclosed no essential pathologic process; although there was possible slight perineuronal vacuolation in the cerebral cortex. Liver sections showed diffuse and focal (portal) chronic inflammation and widespread cytoplasmic vacuolation and areas of hyalinized hepatocytes.

Patterns of self-administration were erratic in that periods of high cocaine consumption were juxtaposed with periods of no intake (FIG. 2). Psychomotor stimulation, anorexia, mydriasis, stereotypy, and convulsions were seen. Monkey 452 chewed the flesh from its fingers.

Food consumption was reduced somewhat during the first few days of cocaine exposure, and thereafter returned to maximum. Weight losses of 17, 10 and 15% were recorded for monkeys 6736, 452, and 6736, respectively, at the end of their exposure to cocaine.

3-Phenoxypyridine monosulfate (CI-844). All four monkeys presented with 0.5 mg/kg/injection increased their self-administration rates compared to saline (FIG. 3). Intake was erratic, ranging between zero and 200 injections per day for 6764, 6762 and 6748. Monkey 6714 progressively increased its intake daily, reaching a peak of about 600 injections on the 11th day. Thereafter, daily self-injection rates for this animal gradually declined (FIG. 3). Emesis, stimulation, ataxia to the point of falling down, and one incident of mydriasis and salivation were observed during periods of highest drug intake. There were only a few days of anorexia in one monkey (6714), and all animals maintained excellent overall health. Weight gains of 12, 12, 9, and 11% were recorded for monkeys 6714, 6764, 6762, and 6748, respectively.

Because 3-phenoxypyridine monosulfate self-administration rates had declined so dramatically at the end of 30 days for monkey 6714 and to a lesser extent for 6762, the dose was increased to 2.0 for five days then lowered to 0.125 mg/kg/injection for five days. Self-injection of 3-phenoxypyridine monosulfate at these unit doses was lower in all four monkeys than was seen during saline availability.

Figure 4A:
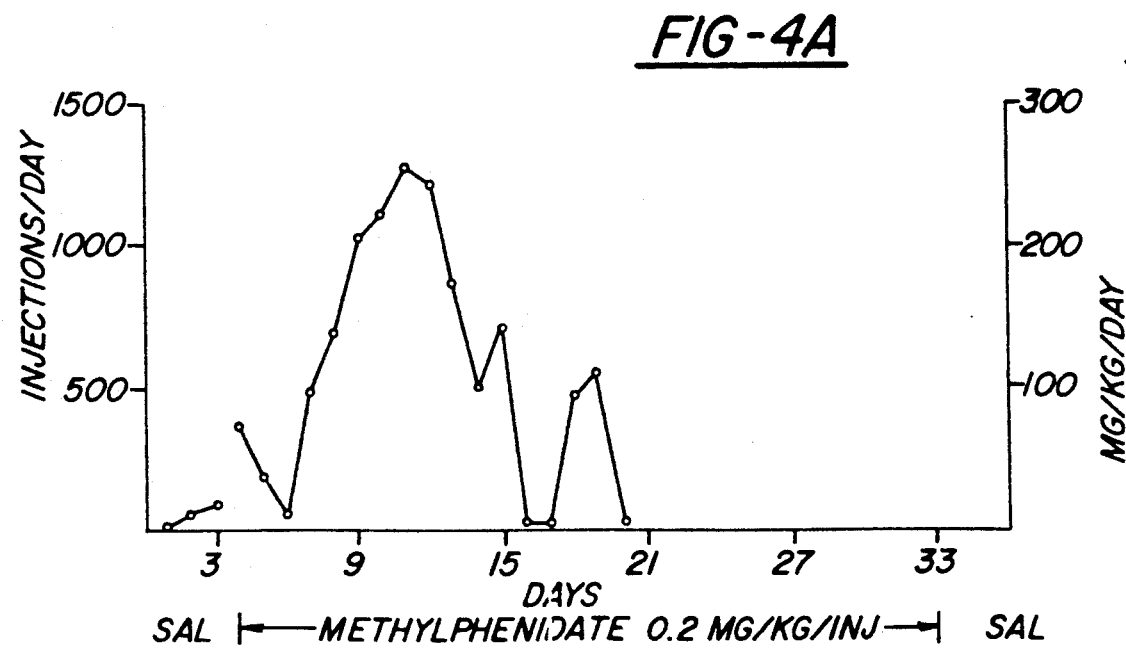
FIG. 4 is a plot of number of injections and total amount of methylphenidate self-administered daily by four rhesus monkeys. Methylphenidate was made available without time or dose limitation for 30 days preceded and followed by three days access to saline. Asterisks denote the deaths of monkeys 468, 6765, and 6731.

Methylphenidate. Four monkeys (468, 6765, 6731, 6782) allowed access to 0.2 mg/kg/injection of methylphenidate showed greatly increased rates of bar pressing compared to saline (FIG. 4). Three of the monkeys (468, 6765, 6731) showed maximum intake between the fifth and tenth day of methylphenidate exposure. Self-injections declined thereafter and all three animals went into brief comas and died within the first 20 days. Prior to death, anorexia and weight losses of 4, 23, and 26% were noted for 468, 6765, and 6731, respectively. Other signs included mydriasis, stimulation, constant locomotion, ataxia, and weakness. The most prominent sign was incessant movement. Lesions formed on the hips and wrists of 6731 from abrasion against the cage floor produced by swimming movements. Lesions occurred on monkey 468 from the harness. These two monkeys became so ataxic and weak that they were unable to drink from the automatic water system and had to be given water in pans.

Monkey 6782 survived the test period showing no anorexia but a 17% weight loss. Despite low methylphenidate consumption and relatively minor behavioral abnormalities, this animal looked emaciated and jaundiced at the end of the study,.

No signs of withdrawal were noted following termination of access to any of the drugs tested.

In order of apparent toxicity among the drugs in the above study was methylphenidate<cocaine<D-amphetamine<3-phenoxypyridine monosulfate. This hierarchy is not solely dependent upon the total amount of drug consumed, since the monkeys took more 3-phenoxypyridine monosulfate overall than either cocaine or amphetamine. Neither it is exclusively related to the unit dose presented for self-administration, since the total daily amount of stimulant drugs taken by monkeys has been shown by a number of investigators to be more or less independent of the dose per injection.

The monkeys which died showed the greatest intensity and persistence of prior psychomotor stimulation. Continuous locomotion, stereotypy, anorexia, weakness, and ataxia were very prominent with methylphenidate and cocaine, and to a lesser degree with amphetamine. The etiology of the morphological changes seen in brains of monkeys which died is not clear. The histopathology may have been drug related, but there was also a correlation between the duration of coma and the extent of cellular change.

The patterns of self-administration and concomitant toxicities seen in the present study have been observed with psychomotor stimulants by other investigators. In contrast, monkeys exposed to 3-phenoxypyridine monosulfate showed little overall toxicity and maintained excellent health. Signs such as stimulation and emesis were observed infrequently and only during periods of maximum drug intake. While 3-phenoxypyridine monosulfate did act as a reinforcer in monkeys and therefore has some potential for human abuse, it was less psychotoxic than the comparison drugs. For this reason, it is considered to be a safer substitute in regard to abuse liability than cocaine, amphetamine or methylphenidate.

The preparation of dosage forms in preferred embodiments is illustrated by the following examples.

Example 1

| Ingredient | Quantity |
| --- | --- |
| 3-Phenoxypyridine Monosulfate | 236 g. |
| Lactose | 1038 g. |
| Corn Starch | 39 g. |
| Hydroxypropyl cellulose | 30 g. |
| Magnesium stearate | 7 g. |
| Ethanol-water 50:50 | q.s. |

The 3-phenoxypyridine monosulfate, lactose and hydroxypropyl cellulose are blended and granulated with 50:50 ethanol-water. The wet granulation is screened, dried an rescreened. The resulting dried granulation is blended with the magnesium stearate and the corn starch, and the mixture is compressed into 225 mg. tablets using 11/32 inch standard concave punches. Yield equals approximately 6,000 tablets, each containing 39.3 mg. of 3-phenoxypyridine monosulfate equivalent to 25 mg. of 3-phenoxypyridine base.

By substituting an equivalent amount of another pharmaceutically acceptable 3-phenoxypyridine salt for the 3-phenoxypyridine monosulfate and adjusting the amount of lactose to give the same total weight in the above formula, there are again obtained 225 mg. tablets each containing the equivalent of 25 mg. of 3-phenoxypyridine base.

Example 2

| Ingredient | Quantity |
| --- | --- |
| 3-Phenoxypyridine Monosulfate | 943 g. |
| Lactose | 1176 g. |
| Corn Starch | 60 g. |
| Hydroxypropyl cellulose | 60 g. |
| Magnesium stearate | 11 g. |
| Ethanol-water 50:50 | q.s. |

The 3-phenoxypyridine monosulfate, lactose and hydroxypropyl cellulose are blended and granulated with 50:50 ethanol-water. The wet granulation is screened, dried and rescreened. The resulting dried granulation is blended with the magnesium stearate and the corn starch, and the mixture is compressed into 375 mg. tablets using 3/32 inch standard concave punches. Yield equals approximately 6,000 tablets, each containing 157.2 mg. of 3-phenoxypyridine monosulfate equivalent to 25 mg. of 3-phenoxypyridine base.

By substituting an equivalent amount of another pharmaceutically acceptable 3-phenoxypyridine salt for the 3-phenoxypyridine monosulfate and adjusting the amount of lactose to give the same total weight in the above formula, there are again obtained 375 mg. tablets each containing the equivalent of 100 mg. of 3-phenoxypyridine base.

| Example 3 | |
|---|---|
| Ingredient | Quantity |
| 3-Phenoxypyridine Monosulfate | 2358 g. |
| Lactose | 444 g. |
| Corn Starch | 90 g. |
| Hydroxypropyl cellulose | 90 g. |
| Magnesium stearate | 18 g. |
| Ethanol-water 50:50 | q.s. |

The 3-phenoxypyridine monosulfate, lactose and hydroxypropyl cellulose are blended and granulated with 50:50 ethanol-water. The wet granulation is screened, dried and rescreened. The resulting dried granulation is blended with the magnesium stearate and the corn starch, and the mixture is compressed into 500 mg. tablets using ½ inch standard concave punches. Yield equals approximately 6,000 tablets, each containing 393 mg. of 3-phenoxypyridine monosulfate equivalent to 250 mg. of 3-phenoxypyridine base.

By substituting an equivalent amount of another pharmaceutically acceptable salt of 3-phenoxypyridine for the 3-phenoxypyridine monosulfate and adjusting the amount of lactose to give the same total weight in the above formula, there are again obtained 500 mg. tablets each containing the equivalent of 250 mg. of 3-phenoxypyridine base.

| Example 4 | |
|---|---|
| Ingredient | Quantity |
| 3-Phenoxypyridine Monosulfate | 393 g. |
| Lactose | 1580 g. |
| Magnesium stearate | 27 g. |

The mixture is blended and filled into No. 4 hard gelatin capsules, filling each capsule with 200 mg. of the powder mixture. Yield equals approximately 10,000 capsules, each containing 39.3 mg. of 3-phenoxypyridine monosulfate equivalent to 25 mg. of 3-phenoxypyridine base.

By substituting an equivalent amount of another pharmaceutically acceptable salt of 3-phenoxypyridine for the 3-phenoxypyridine monosulfate and adjusting the amount of lactose to give the same total weight in the above formula, there are again obtained 200 mg. capsules, each containing the equivalent of 25 mg. of 3-phenoxypyridine base.

| Example 5 | |
|---|---|
| Ingredient | Quantity |
| 3-Phenoxypyridine Monosulfate | 1572 g. |
| Lactose | 1540 g. |

-continued

| Example 5 | |
|---|---|
| Ingredient | Quantity |
| Magnesium stearate | 88 g. |

The mixture is blended and filled into No. 2 hard gelatin capsules, filling each capsule with 320 mg. of the powder mixture. Yield equals approximately 10,000 capsules, each containing 157.2 mg. of 3-phenoxypyridine monosulfate equivalent to 100 mg. of 3-phenoxypyridine base.

By substituting an equivalent amount of another pharmaceutically acceptable salt of 3-phenoxypyridine for the 3-phenoxypyridine monosulfate and adjusting the amount of lactose to give the same total weight in the above formula, there are again obtained 320 mg. capsules, each containing the equivalent of 100 mg. of 3-phenoxypyridine base.

| Example 6 | |
|---|---|
| Ingredient | Quantity |
| 3-Phenoxypyridine Monosulfate | 3930 g. |
| Lactose | 1700 g. |
| Magnesium stearate | 170 g. |

The mixture is blended and filled into No. 0 hard gelatin capsules, filling each capsule with 580 mg. of the powder mixture. Yield equals approximately 10,000 capsules, each containing 393 mg. of 3-phenoxypyridine monosulfate equivalent to 250 mg. of 3-phenoxypyridine base.

By substituting an equivalent amount of another pharmaceutically acceptable 3-phenoxypyridine salt for the 3-phenoxypyridine monosulfate and adjusting the amount of lactose to give the same total weight in the above formula, there are again obtained 580 mg. capsules, each containing the equivalent of 250 mg. of 3-phenoxypyridine base.

| Example 7 | |
|---|---|
| Ingredient | Quantity |
| 3-Phenoxypyridine | 500 g. |
| Polyethylene glycol 400 | 1000 g. |

The above ingredients are blended and filled into soft gelatin capsules, filling each capsule with 300 mg. of the mixture. Yield equals approximately 5,000 capsules, each containing 100 mg. of 3-phenoxypyridine.

PREPARATION OF ACID ADDITION SALTS

A. 3-Phenoxypyridine Hydrochloride

A solution of 10 g. of 3-phenoxypyridine in 10 ml. of 2-propanol is treated with an excess of a solution of dry hydrogen chloride in 2-propanol. The resulting solution is stirred and diluted with ether to give a yellow oil. The oil is separated, triturated several times with ether to give 3-phenoxypyridine hydrochloride as a crystalline solid; m.p. 112°–113.5° C. after recrystallization from 2-propanolether followed by drying at reduced pressure.

B. 3-Phenoxypyridine Hydrobromide

A solution of 85 g. of 3-phenoxypyridine in 100 ml. of absolute ethanol is treated with 84 g. of 48% hydrobromic acid with stirring and the solution is evaporated to dryness at reduced pressure. The residue is dissolved in warm 2-propanol, the solution is diluted to cloudiness with ether and chilled to crystallize 3-phenoxypyridine hydrobromide; m.p. 132°–134° C. after drying at reduced pressure.

C. 3-Phenoxypyridine Nitrate

A solution of 9 g. of 3-phenoxypyridine in 20 ml. of absolute ethanol is treated with 9 g. of 70% nitric acid with stirring. The resulting mixture is diluted with 200 ml. of ether and the crystalline precipitate of 3-phenoxypyridine nitrate is collected by filtration, washed with ether and dried at reduced pressure; m.p. 103.5°–105° C.

D. 3-Phenoxypyridine Methanesulfonate

A solution of 18 g. of 3-phenoxypyridine in 100 ml. of 2-propanol is treated with 9.6 g. of methanesulfonic acid with stirring. The solution is diluted with ether and the crystalline precipitate of 3-phenoxypyridine methanesulfonate is collected, washed with ether and dried at reduced pressure; m.p. 121°–123° C.

E. 3-Phenoxypyridine p-Toluenesulfonate

A solution of 9 g. of 3-phenoxypyridine in 20 ml. of absolute ethanol is treated with a solution of 9.5 g. of p-toluenesulfonic acid monohydrate in 10 ml. of absolute ethanol with stirring. The resulting solution is evaporated at reduced pressure and the residue triturated with ether to crystallize 3-phenoxypyridine p-toluenesulfonate which is collected by filtration and washed with ether; m.p. 78°–80° C. after recrystallization from 2-propanol.

F. 3-Phenoxypyridine Monosulfate

A solution of 523 g. of 3-phenoxypyridine in 750 ml. of 2-propanol is treated slowly with stirring with 303 g. of 98% sulfuric acid, while maintaining the temperature below 50° C. On cooling to room temperature, the mixtures sets up solid. It is heated to 75° C., transferred to an acceptable container and allowed to cool to 50° C. and the crystalline product collected by filtration. The filtrate is allowed to stand at room temperature for 2 hours and the additional crystalline product is collected by filtration. The combined product is dried at reduced pressure to give 3-phenoxypyridine monosulfate, m.p. 103°–107° C. The salt is recrystallized from acetonitrile; after drying at reduced pressure it melts at 107°–109° C.

The embodiments of the invention in which an exclusive property or privilege is claimed are defined as follows.

What is claimed is:

1. A method for reducing or eliminating the abusive use of a psychomotor stimulant compound resulting in psychotoxicity, which method comprises administering in dosage form an effective amount of 3-phenoxypyridine or a pharmaceutically acceptable acid-addition salt thereof to a subject in need of reducing said use.

2. The method of claim 1 for reducing the use of a psychomotor stimulant compound selected from the group consisting of cocaine, amphetamine and methylphenidate.

3. The method of claim 1 including the step of orally administering to the subject spaced daily doses of said compound ranging from about 0.1 to about 400 mg/kg of body weight.

4. The method of claim 3 wherein the doses are taken four times daily.

5. The method of claim 3 wherein the step of administering the compound is continued daily until said abusive use is controlled up to a maximum daily dosage of about 1600 mg/kg of body weight.

* * * * *

UNITED STATES PATENT AND TRADEMARK OFFICE
CERTIFICATE OF CORRECTION

PATENT NO. : 5,232,934
DATED : August 3, 1993
INVENTOR(S) : Downs

It is certified that error appears in the above-identified patent and that said Letters Patent is hereby corrected as shown below:

Column 1, line 43, delete "4,128,555";

Column 2, line 3, delete "465" and insert --452--;

Column 5, line 55, delete "<" and insert -- > --;

Column 5, line 55, after "cocaine", delete "<" and insert -- > --;

Column 5, line 56, delete "<" and insert -- > --;

Column 6, line 37, delete "an" and insert --and--;

Column 6, line 68, delete "3/32" and insert --13/32--.

Signed and Sealed this

Twenty-sixth Day of April, 1994

Attest:

BRUCE LEHMAN

Attesting Officer     *Commissioner of Patents and Trademarks*